United States Patent
Beavers et al.

(10) Patent No.: US 7,320,690 B2
(45) Date of Patent: Jan. 22, 2008

(54) IOL INSERTION DEVICE WITH LUBRICIOUS COATING

(75) Inventors: Ellington M. Beavers, Meadowbrook, PA (US); Elizabeth Pervin, Philadelphia, PA (US); William J. Work, Huntingdon Valley, PA (US)

(73) Assignee: Biocoat Incorporated, Horsham, PA (US)

( * ) Notice: Subject to any disclaimer, the term of this patent is extended or adjusted under 35 U.S.C. 154(b) by 629 days.

(21) Appl. No.: 10/845,472

(22) Filed: May 13, 2004

(65) Prior Publication Data

US 2005/0256528 A1 Nov. 17, 2005

(51) Int. Cl.
*A61F 9/00* (2006.01)
(52) U.S. Cl. ..................................... 606/107
(58) Field of Classification Search ........ 606/107–166; 623/6.11, 6.12; 604/272, 521, 523
See application file for complete search history.

(56) References Cited

U.S. PATENT DOCUMENTS

| | | |
|---|---|---|
| 4,681,102 A | 7/1987 | Bartell |
| 4,801,475 A | 1/1989 | Halpern |
| 5,023,114 A | 6/1991 | Halpern |
| 5,037,677 A | 8/1991 | Halpern |
| 5,716,364 A | 2/1998 | Makker |
| 5,803,925 A | 9/1998 | Yang |
| 5,947,976 A | 9/1999 | Van Noy |
| 5,976,150 A | 11/1999 | Copeland |
| 6,565,584 B1 * | 5/2003 | Mathis et al. ................ 606/166 |

* cited by examiner

*Primary Examiner*—Kevin T. Truong
(74) *Attorney, Agent, or Firm*—William H. Eilberg

(57) ABSTRACT

An insertion device for an intra-ocular lens (IOL) has a bilaminar, lubricious coating on the surface which contacts the IOL as it is being inserted into the eye. The bilaminar coating includes a highly lubricious top coat, and a polymeric base coat which is both highly adherent to the surface of the insertion device, and which has functional groups capable of grafting the base coat to the top coat. In its completed form, the bilaminar coating is essentially permanent, and exceedingly lubricious when wet, allowing the IOL to be advanced smoothly and without damage through the insertion device. The top coat may include hyaluronan, or another material capable of providing the required lubricity.

22 Claims, No Drawings

IOL INSERTION DEVICE WITH LUBRICIOUS COATING

BACKGROUND OF THE INVENTION

The present invention relates to the field of insertion of intra-ocular lenses, and provides an improved device for inserting an intra-ocular lens into the eye.

The original intra-ocular lens (IOL) introduced in 1948 was made of poly(methyl methacrylate), with polypropylene haptics. It was rigid and inflexible and its insertion required a 7 to 9 mm incision in the eye and a stitch to close the wound, with attendant discomfort and the inconvenience of later stitch removal.

With the advent of flexible IOLs made of silicone or acrylate elastomers, which could be folded and inserted into the eye through an incision that might be as small as 2.8 mm or less, no stitch was necessary and the whole procedure was simplified and abbreviated.

The use of flexible IOLs created a need for a device that could guide the lens into the smaller opening in the eye. One example of a device for insertion of an IOL is given in U.S. Pat. No. 4,681,102. Other devices for accomplishing the insertion are described in U.S. Pat. Nos. 5,716,364, 5,803,925, 5,947,976, and 5,976,150. The disclosures of all of the above-cited patents are incorporated by reference herein.

The basic principle embodied in the design of any of the devices shown in the above-cited patents is to provide a lubricious pathway for a folded IOL to be pushed without damage into the corneal chamber (often described as "the bag") from which the eye's natural lens has been removed, where the IOL can unfold spontaneously.

Clearly, many variations are possible in the mechanical design of the apparatus that could carry out the insertion of an IOL satisfactorily, embodying the above-cited principle.

The insertion device, usually formed from plastic and often from polypropylene, comprises a channel that at the proximal end is open, and communicates with a tubular channel that extends to a distal open end. In the operation of some insertion devices, the flexible IOL is placed in the open end of the channel in a folded configuration. In other insertion devices, the IOL becomes folded as a result of design features in the channel that promote folding. The distal end of the device is positioned at the incision in the eye and the IOL pushed through the channel and into the eye. In the presentation that follows, the untreated plastic device will be referred to as the "cartridge".

The requirement that the IOL be moved through the device without damage is critically important, and a corollary requirement is that the passageway be adequately lubricated to reduce friction to a harmless level. The friction to be overcome is jointly characteristic of the IOL and haptic surfaces on the one hand, and the surface of the inner wall of the channel through which the lens is moved on the other hand; i.e., friction cannot be defined as a property of a single surface, but of both surfaces, either or both of which may be moving to generate the friction.

The problem of lubricating the insertion channel has been addressed, to some extent, in the prior art, including some of the patents cited above. For example, U.S. Pat. No. 4,681,102 briefly describes treating the lumen through which the IOL passes with a product known by the trademark Healon. Healon is a solution of sodium hyaluronate in water. A problem with the latter approach is that the Healon can be harmful if introduced into the eye, and not completely removed after the IOL is inserted.

U.S. Pat. No. 5,716,364 also is concerned with lubricating the interface between IOL and the cartridge wall, so as to reduce friction in the movement of the folded IOL. The patent describes the use of lubricants that are not covalently bonded to the surface of the inserter, such as glyceryl monostearate or polyvinylpyrrolidone (PVP). The lubricant is said to be incorporated uniformly throughout the polypropylene, presumably by mixing and compounding in an extruder or milling on plastics processing rolls, and because the lubricant and polypropylene are mutually incompatible, the lubricant blooms to the surface of the cartridge, where it acts to facilitate the passage of the IOL. For the very reason that the lubricant is not bonded chemically to the polypropylene and is therefore mobile and capable of moving to the surface of the cartridge wall, it can be carried along with the IOL and some of it also inserted into the eye. Either glyceryl monostearate or PVP is foreign contamination of the viscous fluid that fills the eye, and whether it will cause long-term problems can only be determined by years of clinical experience.

The same U.S. Pat. No. 5,716,364 also describes a covalently bonded lubricity enhancing component, but no teaching is made in this patent as to how glyceryl monostearate or PVP might be covalently bound to polypropylene.

In U.S. Pat. No. 5,803,925, the subject is an IOL inserter with a covalently bound lubricant of the type represented by the formula A-PEG, where A is a reactive group capable of bonding chemically to the surface of the cartridge, and PEG is polyethylene glycol or other hydrophilic (or oleophilic) polymer. In the operation of the inserter, the clean cartridge is soaked for about three hours in a solution of the A-PEG and is then subjected to UV irradiation to cause photolysis of the polypropylene and bonding of the A-PEG.

The covalently bonded and immobile "lubricant" does not lubricate adequately to facilitate the passage of the IOL through the pathway of the device. The patent states that a balanced salt solution of sodium hyaluronate (BSS) must be used along with the treated inserter in order to achieve sufficiently low friction for the IOL to pass, with the normal application of force. The patent reports the finding that neither the cartridge with bonded A-PEG but without BSS, nor the untreated cartridge with BSS alone, is effective in passing the folded IOL The present invention comprises an IOL insertion device having a continuous, bilaminar, lubricious coating which is permanently bound to at least a portion of the inner surface of the channel through which an IOL passes. The coatings used with the insertion device of the present invention have been found to produce results that are superior to those of any of the known IOL insertion devices of the prior art.

SUMMARY OF THE INVENTION

The present invention comprises an insertion device for an intra-ocular lens (IOL), the insertion device defining a channel through which the IOL is advanced while inserting it into an eye. At least the interior surface of the insertion device, i.e. the surface which contacts the IOL during the insertion process, has a bilaminar coating. The bilaminar coating includes a highly lubricious top coat which is chemically grafted to a base coat, the base coat firmly adhering to the surface of the insertion device. The base coat comprises a polymer which includes functional groups capable of participating in reactions for grafting the base coat to the top coat.

The top coat is preferably a solution of a polymer selected from the group consisting of a polysaccharide, a cellulose derivative, polyacrylic acid, and polyethylene glycol. The preferred top coat is an aqueous solution of hyaluronan. The top coat may also include surfactants, crosslinking agents, plasticizers, solvents, salts, and/or leveling agents.

The base coat comprises a polymer or copolymer capable of providing adhesion to the substrate surface. Preferably the base coat is selected from the group consisting of acrylic polymers and acrylic copolymers.

The insertion device is preferably made of a moldable material, such as plastic. More particularly, the moldable material can be selected from the group consisting of polypropylene, acrylic polymers, acrylic copolymers, nylon, polyester, cellulose acetate, and acetate/butyrate.

When the channel is wet with water, the insertion device described above provides an extremely lubricious interface between the IOL and the channel. The coating applied to the insertion device is permanent, and does not become dislodged as the IOL is advanced into the eye.

The invention also comprises a method of enhancing the lubricity of an insertion device for an IOL, the method including applying a bilaminar coating of the kind described above, to at least a portion of the interior surface of the insertion device.

The present invention therefore has the primary object of providing an insertion device for an intra-ocular lens (IOL).

The invention has the further object of providing an insertion device for an IOL which substantially reduces the friction between the IOL and the insertion device, as the IOL is advanced into an eye.

The invention has the further object of providing an insertion device having a permanent coating that becomes exceedingly lubricious when wet with water.

The invention has the further object of preventing unwanted substances from entering the eye during the process of insertion of an IOL.

The invention has the further object of enhancing the safety of an IOL insertion procedure.

The invention has the further object of providing a method of enhancing the lubricity of an insertion device for an IOL.

The reader skilled in the art will recognize other objects and advantages of the present invention, from a reading of the following detailed description of the invention, and the appended claims.

DETAILED DESCRIPTION OF THE INVENTION

The present invention is based on the discovery that a continuous, lubricious coating, permanently bound to an IOL insertion device, is more effective in facilitating passage of the IOL than a covalently bonded lubricant, does not contaminate the eye with foreign matter, and is superior in having other unexpected advantages, as will be described. Coatings made according to the present invention have demonstrated excellent performance in practical experience of providing lubricity for vascular catheters and guide wires, with unexcelled biocompatibility and freedom from undesirable side effects. Their adaptability to an IOL insertion device comprising a polypropylene cartridge, and the consequent virtues in such an application, were unforeseen and not predictable.

The coatings used in the present invention are bilaminar, hydrophilic, lubricious coatings formed on substrates which are typically plastic. Such coatings are described in U.S. Pat. Nos. 4,801,475, 5,023,114, and 5,037,677, the disclosures of which are hereby incorporated by reference. In general, these patents disclose bilaminar coatings comprising a primary or base coat that adheres tightly to a plastic substrate, and a top coat which is hydrophilic, lubricious and durable. In one preferred embodiment, the top coat is a polysaccharide such as hyaluronan. The primary coat and the top coat are grafted together with covalent bonds, and retain their individual identities even after grafting. The base coat is sometimes called a "tie-coat" because it ties the top coat to the substrate.

In the coatings described in the above-cited patents, the primary coat and the top coat are grafted together with covalent bonds, and retain their individual identities even after grafting. The above-cited patents teach that these bilaminar coatings can be used on catheters, guide wires, prosthetic devices, or intra-ocular lenses. However, none of these patents discloses or suggests the use of such coatings on an interior surface of a channel used for insertion of an IOL.

As in the above-cited patents, the coatings used in the present invention are bilaminar, comprising a base coat that is 1) highly adherent to polypropylene and 2) functional in the sense of being able to participate in reactions with agents for grafting the base coat to a suitable lubricious top coat. Materials and conditions of application are specifically chosen and designed to effect maximum adhesion of the coating to the surface of the IOL insertion cartridge. The successful achievement of this objective, as will be demonstrated, is a fundamental virtue of this family of coatings.

The base coat may be a polymer or copolymer supplied as a solution in a suitable organic solvent or supplied in the form of an aqueous colloidal dispersion or emulsion or non-aqueous dispersion. The material as supplied may be diluted at the time of use and otherwise formulated with the polyfunctional reagent that will serve to tie the two coats together with chemical bonds, and, in the judgment of the experienced formulator, treated perhaps with a leveling agent and/or a wetting agent, and/or other agents well known in the art that facilitate the formation of stable, uniform, well-adhering coatings.

The top coat is usually a lubricious water-soluble polymer that can be a polysaccharide, such as hyaluronan, a cellulose derivative, polyacrylic acid and its water soluble copolymers, polyethylene glycol, and the like. The top coat may also be formulated, by dilution and by the addition of surfactant, crosslinking agent, plasticizer, solvent, salts, or leveling agent, and/or other agents that improve the coating and the coating process.

Clearly the interior surface of the device, through which the IOL is to be inserted, must be immaculately clean and free of oils, greases and dirt. Cleaning, etching, and surface modification by chemical or plasma treatment is especially recommended. Other surface treatments accomplishing similar effects may consist of exposure to an oxidizing acidic reagent such as chromic acid, or corona treatment, or combinations thereof.

The coating may be applied to the entire device or, preferably, to the inside surface only, and in some cases only to preferred specific areas of the interior of the device, such as the channel of diminished diameter through which the IOL must travel just before entering the eye. There may also be specialized tools to facilitate the entry of the IOL into the incision and into the "bag", that might benefit from being coated also.

The formulated base coat may be applied by any convenient method, such as by dipping, spraying, brushing, filling and draining, or by injection from a pipette or other liquid dispenser. During the application of the fluid coatings, drying, and curing, the device may be seated in a bottomless, suitably formed receptacle, or held by friction fit in the open end of a cylindrical tube fitted at the other end in a gas manifold, or by other suitable means. Passing clean dry air, nitrogen, or other inert gas through the device during drying and curing may be desirable as a means of accelerating removal of solvents and other volatile matter.

After application of the base coat, the device is heated for a brief period, the duration of which depends upon temperature and rate of gas passage over the surface, to remove volatiles. The top coat is then applied by methods similar to those used for the base coat, and heating resumed to remove volatiles and to bring about the grafting reaction between base coat and top coat. At the end of the curing cycle, the coated devices are cooled and then soaked briefly in dilute aqueous $NaHCO_3$ or other dilute weak base, washed with sterile water and dried.

The coating made according to the present invention shows exquisite lubricity when it is wet simply with water and/or other aqueous solutions.

The following examples illustrate the operation of the invention, but should not be construed to limit the invention.

EXAMPLE 1

After plasma treatment in oxygen, polypropylene cartridges were immersed and gently agitated for 3 minutes in a base coat formulation comprising 100 grams of HYDAK B-23K, 6.87 grams of DESMODUR N-75, and 306.7 grams of HYDAK PMA. HYDAK is a registered trademark of Biocoat Incorporated, of Fort Washington, Pa., and DESMODUR is a registered trademark of Bayer AG. The HYDAK B-23K and HYDAK PMA pertain to the acrylic base coat polymer solution or emulsion, and the trademark DESMODUR pertains to a polyisocyanate cross-linker. The combination of the above ingredients constitutes the base coat.

The isocyanate serves two purposes. First, it crosslinks the base coat polymer. Secondly, it provides isocyanate groups on the surface of the base coat which are used to tie the top coat to the base coat.

Each wet device was then attached by friction fit at its distal end to the open end of plastic tubing through which dry air was flowing from a manifold. The temperature of the assembly was raised and held at 60° C. for 20 minutes. The assembly was removed from the oven and allowed to cool for 10 minutes. Air flow was stopped temporarily while the top coat, HYDAK L-110, a solution of hyaluronan, was applied by syringe for the interior length of the device channel. Air flow was restarted, and after 20 to 30 seconds any excess top coat solution that had accumulated at the bottom edge was dabbed off with filter paper. The temperature was raised again to 60° C. and held for 2 hours. After cooling, the devices were removed from the assembly and soaked for 15 minutes in dilute $NaHCO_3$, having a concentration of about 0.5%. The concentration need not be precisely 0.5%, but could be in a range of about 0.2 to about 1.0% (w/w). After washing with sterile water and drying, the coated devices were ready for packaging and sterilization.

When one of these coated devices was immersed briefly in sterile water and then tested with an IOL, the technician reported that the IOL passed through the channel with almost no resistance. In fact, he expressed the opinion that he might feel in better control if slightly higher friction were encountered, but that with further experience he might adjust to the unusual behavior.

EXAMPLE 2

As a demonstration of the durable security of the coating applied as in Example 1, the formulation and procedures described there were replicated with coatings on one side of each of two polypropylene panels measuring 2.75×6.75×0.25 inches. The panels were mounted, with the coated side facing upward, in a BYK Gardner Abrasion Tester (part No. LAG-8100, available from BYK Gardner USA, of Columbia, Md.), which complies with ASTM method D 2486. While the panels were immersed in deionized water, a brush with stiff nylon bristles under a weight of 450 grams was drawn over the coated surfaces at a rate of 37 cycles per minute. After more than three hundred thousand cycles (more than 600,000 strokes), the coatings had undergone no change: they were still as lubricious as at the start of the test, and the coating had not lost adhesion, flaked, whitened, nor blistered or shown signs of failure of any kind whatever.

Although polypropylene is an attractive material of construction for the IOL insertion device, because of its low cost, inert character, and well known behavior in conventional molding and processing operations, the uncoated cartridge could be molded from acrylic polymers and copolymers of suitable softening point, nylon, polyester, cellulose acetate or acetate/butyrate, or other moldable polymers well known in the art, and when coated as described here, would serve with virtually identical properties.

In summary, the IOL insertion device of the present invention is superior to any known heretofore, capable of conveying a foldable IOL with minimum force, without damage, into the eye through a small incision. The channel through which the IOL passes is highly lubricious when wet with water.

The bilaminar coating formed on the surface of the insertion device is permanent, and does not become dislodged when the IOL is inserted into the eye. Thus, the danger of introducing a foreign lubricant into the eye, during the IOL insertion process, can be eliminated.

The insertion device, with its lubricious coating, is stable in storage and resistant to abuse, simple in operation, difficult to misuse, and biocompatible.

The invention can be modified in many ways, within the scope of the preceding disclosure. The specific choice of materials for the base coat and top coat can be varied, as described above. The bilaminar coating may be applied to the entire surface of the IOL insertion device, or it may be applied only to the interior surface defining the channel through which the IOL passes. The coating may also be applied only in the portion of the insertion device having a reduced diameter, where the friction between the insertion device and the IOL is likely to be greatest. These and other modifications, which will be apparent to those skilled in the art, should be considered within the spirit and scope of the following claims.

What is claimed is:

1. In an insertion device for an intra-ocular lens (IOL), the insertion device including a channel through which an IOL can be advanced while inserting the IOL into an eye, the channel having an interior surface which contacts the IOL, the improvement wherein at least a portion of the interior surface of the channel has a bilaminar coating, the coating including a lubricious top coat, and a base coat which is chemically grafted to the top coat, wherein the base coat adheres to the interior surface of the channel without being covalently bonded to said surface, the base coat including functional groups capable of participating in reactions for grafting the base coat to the top coat.

2. The improvement of claim 1, wherein the top coat comprises a lubricious, water-soluble polymer.

3. The improvement of claim 2, wherein the polymer defining the top coat is selected from the group consisting of a polysaccharide, a cellulose derivative, polyacrylic acid and its water-soluble copolymers, and polyethylene glycol.

4. The improvement of claim 1, wherein the top coat comprises hyaluronan.

5. The improvement of claim 1, wherein the top coat includes at least one material selected from the group consisting of surfactants, crosslinking agents, plasticizers, solvents, salts, and leveling agents.

6. The improvement of claim 1, wherein the base coat comprises a polymer or copolymer supplied in an organic solvent.

7. The improvement of claim 1, wherein the base coat comprises a polymer or copolymer supplied as an aqueous colloidal dispersion or emulsion or a non-aqueous dispersion.

8. The improvement of claim 1, wherein the insertion device is made of a material selected from the group consisting of polypropylene, acrylic polymers, acrylic copolymers, nylon, polyester, cellulose acetate, and acetate/butyrate.

9. An insertion device for an intra-ocular lens (IOL), comprising a moldable material defining a lumen through which the IOL can be advanced, the lumen being bounded by an interior surface of said moldable material, at least a portion of the interior surface having a bilaminar coating, the coating including a lubricious top coat, and a base coat which is chemically grafted to the top coat, wherein the base coat adheres to said interior surface without being covalently bonded to said surface, wherein the base coat includes functional groups capable of participating in reactions for grafting the base coat to the top coat.

10. The insertion device of claim 9, wherein the top coat comprises a water-soluble polymer selected from the group consisting of a polysaccharide, a cellulose derivative, polyacrylic acid and its water-soluble copolymers, and polyethylene glycol.

11. The insertion device of claim 9, wherein the top coat comprises hyaluronan.

12. The insertion device of claim 9, wherein the top coat includes at least one material selected from the group consisting of surfactants, crosslinking agents, plasticizers, solvents, salts, and leveling agents.

13. The insertion device of claim 9, wherein the base coat comprises a polymer or copolymer supplied in an organic solvent.

14. The insertion device of claim 9, wherein the base coat comprises a polymer or copolymer supplied as an aqueous colloidal dispersion or emulsion or a non-aqueous dispersion.

15. The insertion device of claim 9, wherein the moldable material is selected from the group consisting of polypropylene, acrylic polymers, acrylic copolymers, nylon, polyester, cellulose acetate, and acetate/butyrate.

16. A method of enhancing the lubricity of an insertion device for an intra-ocular lens (IOL), the insertion device including a channel having an interior surface along which the IOL is advanced, the method comprising applying a bilaminar coating to at least a portion of said interior surface, the bilaminar coating including a base coat and a top coat, the base coat being adherent to said interior surface without being covalently bonded to said surface, the base coat having functional groups which enable the base coat to become chemically grafted to a top coat, the top coat being lubricious.

17. The method of claim 16, wherein the applying step is preceded by the step of cleaning said interior surface.

18. The method of claim 16, wherein the applying step includes selecting the top coat from the group consisting of a polysaccharide, a cellulose derivative, polyacrylic acid and its water-soluble copolymers, and polyethylene glycol.

19. The method of claim 16, wherein the applying step includes selecting the top coat to be hyaluronan.

20. The method of claim 16, wherein the applying step includes selecting the top coat to include at least one material selected from the group consisting of surfactants, crosslinking agents, plasticizers, solvents, salts, and leveling agents.

21. The method of claim 16, wherein the applying step includes selecting the base coat to include a polymer or copolymer supplied in an organic solvent.

22. The method of claim 16, wherein the applying step includes selecting the base coat to include a polymer or copolymer supplied as an aqueous colloidal dispersion or emulsion or non-aqueous dispersion.

* * * * *